United States Patent [19]
Vogler et al.

[11] Patent Number: 5,187,727
[45] Date of Patent: Feb. 16, 1993

[54] METHOD AND APPARATUS FOR MEASURING THE IRON CONTENT IN ZINC LAYER AND THICKNESS OF ZINC LAYER

[76] Inventors: Friedrich Vogler, Aschaffenburger Str. 37; Hanns-Werner Ortner, Agnes-Miegel-Strasse 3; Matthias Mayerhofer, Gerhard-Hauptmann-Str. 11, all of D-8520 Erlangen, Fed. Rep. of Germany

[21] Appl. No.: 726,585

[22] Filed: Jul. 8, 1991

[30] Foreign Application Priority Data

Jul. 6, 1990 [DE] Fed. Rep. of Germany ....... 4021617

[51] Int. Cl.$^5$ ............................................. G01B 15/02
[52] U.S. Cl. .................................... 378/50; 378/46; 378/89
[58] Field of Search ................ 378/44, 45, 46, 50, 378/86, 88, 89, 90

[56] References Cited

U.S. PATENT DOCUMENTS

| | | | |
|---|---|---|---|
| 3,012,140 | 12/1961 | Pellissier et al. | 378/50 |
| 3,843,884 | 10/1974 | Evans | 378/50 |
| 3,848,125 | 11/1974 | Utt et al. | 378/50 |
| 4,748,647 | 5/1988 | Kaiser et al. | 378/50 |
| 4,764,945 | 8/1988 | Tadahiro | |
| 4,959,848 | 9/1990 | Parobek | 378/50 |

FOREIGN PATENT DOCUMENTS 3031046 4/1982 Fed. Rep. of Germany .
3718245 12/1987 Fed. Rep. of Germany .
263673 1/1989 Fed. Rep. of Germany .

OTHER PUBLICATIONS

Prospekt der Fa. Siemens "Systeme für die energiedispersive Analyse," 1974 J. Seda et al., Verminderung des statistischen Fehlers bei Messungen von Auflageschichten mittels Röntgenfluoreszenzstrahlung.

Primary Examiner—David P. Porta
Attorney, Agent, or Firm—Ostrolenk, Faber, Gerb & Soffen

[57] ABSTRACT

A method and apparatus for measuring, for example, the iron content in zinc layers and/or the thickness of a layer of zinc in galvanized steel. In order to measure the percentage of iron content in a zinc layer, the apparatus has a source of X-radiation which is arranged at a specified angle to the plane of the material to be measured and at least two detectors equipped with selective sensitivity, one of which is arranged at a second angle and the other at a third angle. One detector measures the iron content and the other detector measures essentially the amount of zinc per unit surface of the coating. From these two measurements, the amount of iron as a percentage of the zinc layer can be calculated.

29 Claims, 2 Drawing Sheets 5,187,727

METHOD AND APPARATUS FOR MEASURING THE IRON CONTENT IN ZINC LAYER AND THICKNESS OF ZINC LAYER

BACKGROUND OF THE INVENTION

The present invention relates to a method and apparatus for measuring the iron content in layers of zinc and/or the thickness of the layer of zinc in the case of galvanized steel by the use of a source of X-rays and a radiation detector. In the production of steel, strip steel is coated with zinc in order to increase its corrosion resistance. This coating is effected, for instance, in a so-called galvannealing process, i.e. by subsequently heating the galvanized steel to about 500° to 600° C. As a result of this "galvannealing," iron diffuses into the layer of zinc so that intermetallic bonds between zinc and iron are formed. This intermetallic bond is of extremely great importance for the further workability of the coated steel and the adherence of the layer of zinc. In this connection, it is particularly important to adjust the proportion of iron in the zinc layer within narrow limits during the manufacturing process, for which purpose the precise percentages of the amount of iron in the layer of zinc must be known in each case. In order to determine this percentage of iron or to measure the iron content in the zinc layer, a method of measuring the crystallographic lattice constants for the Fe/Zn crystallization by the Bragg method has been described by Kawasak Seitetsu Giho under the title "Continuous Measurement of Fe Content in Galvannealed Coating," dated Jan. 28, 1988. However, this method is suitable only for the laboratory, since the expense for apparatus is very high, the measurement times are relatively long, namely more than 20 seconds, and a change in position of the material being measured leads to erroneous measurement results.

A method is also known in which a material radiation excitation is produced by an X-ray radiator so that an energy-selective measurement of the percentages of zinc and iron can be effected by means of a proportional counter. This method has been described by Schikawa Works Nisshin Steel Co. Ltd., Japan, under the title "Measuring the Degree of Alloying of Galvannealed Steel Sheets by X-ray Diffraction Technique and Its Practical Use." By this method, the proportional counter (detector) is brought during the measurement process at different angles to the surface of the material being measured so that the crystal structure can be determined from these measurement results. In this connection, very considerable problems as to stability arise so that, for instance, the mere movement of the material being measured, i.e. the movements of the material around the resting surface, necessarily leads to erroneous measurements. Thus, this method also is merely suited for the laboratory.

None of the methods known up to now for measuring the content of iron in zinc layers in galvanized steel is suitable for use for measurements during the production process in order thus to note the actual value, so that the process control can be carried out accordingly.

SUMMARY OF THE INVENTION

Therefore, an object of the present invention is to provide a method and apparatus for measuring the iron content of zinc layers on steel.

It is a further object to provide a method and apparatus for measuring the thickness of a zinc layer on galvanized steel.

It is furthermore an object of the present invention to provide a method and apparatus by which the existing measurement values of the coating are ascertained during the rough course of production, i.e., in an "on-line" process.

The above and other objects are achieved in accordance with one aspect of the invention by an apparatus having a measurement head in which there are provided a high-voltage source of X-radiation disposed at an angle of between 60° and 120° to the plane of the material to be measured and at least two detectors of selective sensitivity, one of the detectors being arranged at an angle of at most 30° thereto and the other detector at an angle of between 60° and 120°.

This measurement apparatus makes it possible, in a so-called on-line operation, to carry out the measurements directly after the application of the layer of zinc such that the iron content in the layer of zinc is determined. At the same time, the thickness of the layer of zinc can also be measured and indicated.

The above and other objects are achieved according to another aspect of the invention by an apparatus receiving a material comprising a layer on a base, and for measuring the percentage content of a first component in the layer, the layer comprising primarily a second component and being disposed in a plane, the base comprising at least in part the first component, the apparatus comprising:

means for producing radiation and directing said radiation at said material such that said radiation will excite said material to produce characteristic emissions at particular frequencies for each of the first and second components, said means for producing radiation being disposed at a first specified angle to the plane of said material;

a first detector disposed at a second specified angle, said first detector receiving said characteristic emission from said material such that a characteristic emissions from said second component is substantially damped in said material, and such that said first detector detects substantially only a characteristic emission from said first component, thereby detecting the amount of said first component in said layer;

a second detector disposed at a third specified angle for receiving and detecting said characteristic emission from said material such that said characteristic emissions from said first component is damped, the amount of said damping being related to and determining substantially the amount of said second component in said material; and means receiving signals from said first and second detectors for determining the percentage of said first component in said layer as a function of said signals.

The above and other objects are achieved according to a further aspect of the invention by an apparatus receiving n material disposed in a plane comprising a layer on a base and for measuring the thickness of the layer, the base comprising a first component and the layer comprising a second component, the apparatus comprising:

means for producing radiation and directing said radiation at said material such that said radiation will excite said material to produce characteristic emissions at particular frequencies for each of the first and second components, said means for producing radiation being disposed at a first specified angle to the plane of said material; and a first detector disposed at a second specified angle, said first detector receiving said characteristic emissions from said material such that a characteristic emission from said first component is damped in said layer of said second component before being received by said first detector, the amount of said damping being related to and determining substantially the amount of said second component and thereby the thickness of said second component.

Methods in accordance with the invention will also be described.

BRIEF DESCRIPTION OF THE DRAWINGS

One illustrative embodiment of the device of the invention is shown diagrammatically in the drawings, in which.

DETAILED DESCRIPTION

Figure 1:
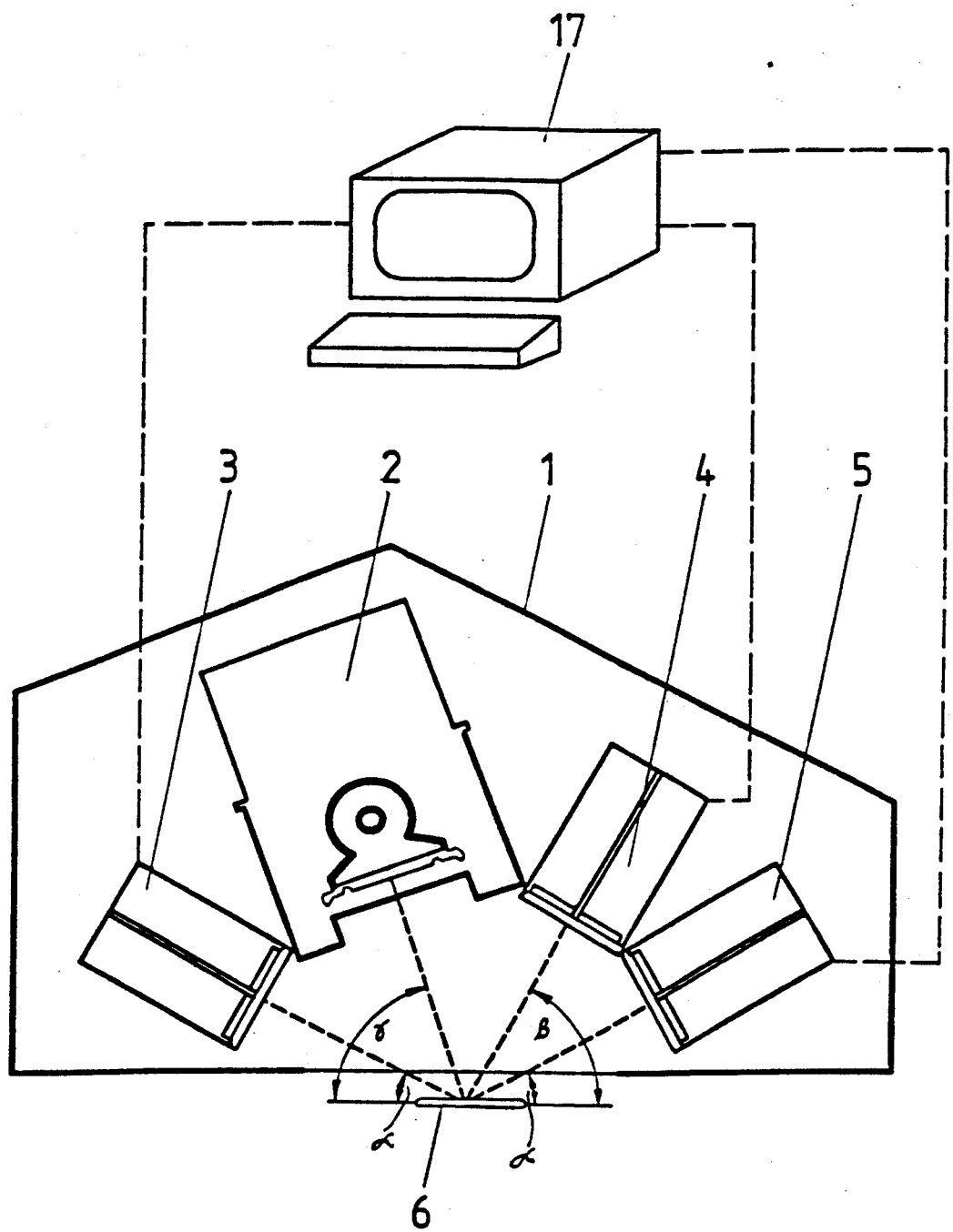
FIG. 1 is a cross section through the device.

With reference now to the drawings, the device according to the invention includes a measurement head 1 having a high-voltage source of X-radiation 2 as well as at least two detectors 3 and 4. A third detector 5 is used when given production conditions or production measures require this, as described further below.

The source 2 of X-radiation is fastened at an angle gamma to the plane of the material 6 being measured (galvanized steel), while the detectors 3 and 5 are arranged at the angle alpha, and the detector 4 at the angle beta, to the plane of the material 6 to be measured. The angle gamma is between 60° and 120°, the angle alpha is at most 30°, and the angle beta is also between 60° and 120°.

The detectors 3, 4 and 5 are developed as detectors of selective sensitivity; this means that these detectors convert the intensity of a given type of ionizing radiation (selectively) into an electric signal and thus make it measurable.

The detectors 3, 4 and 5 detect the characteristic K-lines of Zn (zinc) and Fe (iron), in which connection either suitable absorption filters or pulse discrimination is used in order to achieve the selective sensitivity. Structural shapes of detectors which can be used are explained with reference to FIGS. 2, 3 and 4.

Figure 2:
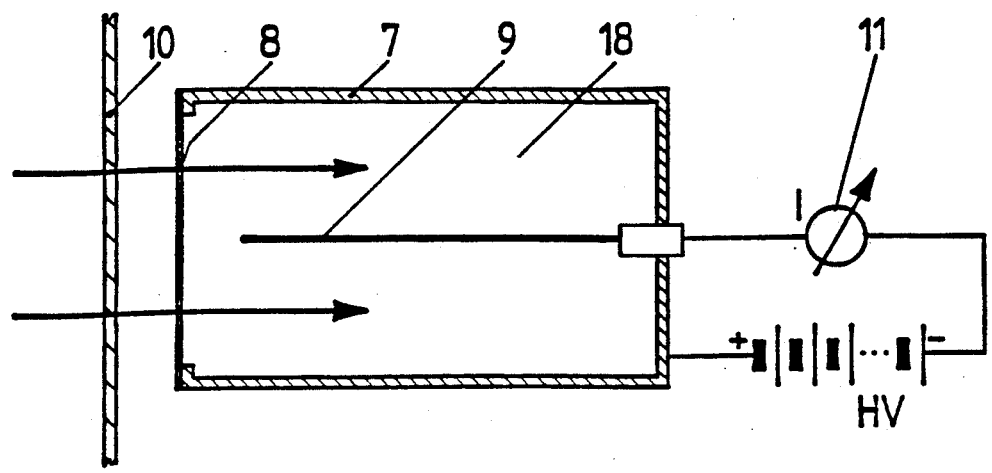
FIG. 2 is a cross section through an ionization-chamber detector with absorption filter.

The detector shown diagrammatically in FIG. 2 consists of a metal housing 7 which is filled with inert gas and referred to as ionization chamber 18. The housing 7 is provided with an entrance window 8, consisting, for instance, of plastic foil. Within the housing 7—and insulated from the housing 7—one or more metal electrodes 9 are arranged. High voltage is applied during the operation between the electrodes 9 and the housing 7.

If ionizing radiation now enters the housing 7 through the entrance window 8, it produces a measurable flow of current at the electrodes 9 by drift of the charge carriers within the electric field generated by the high voltage, the current being measurable by a sensitive ammeter 11. This flow of current reflects the intensity of the radiation. The selective sensitivity of the detector is obtained by applying a corresponding metal foil 10, as absorption filter, in front of the entrance window 8.

Such absorption filters consist, for instance, of copper, iron or other suitable metals.

Figure 3:
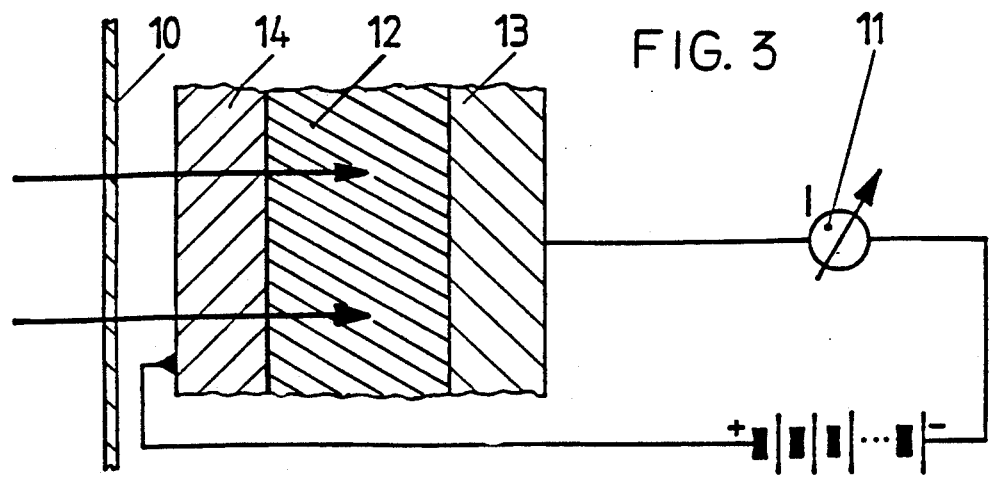
FIG. 3 is a cross section through a semiconductor-diode detector with absorption filter.

FIG. 3 shows a semiconductor-diode detector having p- conductive and n-conductive zones 13 and 14, the selective sensitivity of which is also produced by applying a metal foil 10 in front of the diode. In similar fashion to the ionization-chamber detectors shown in FIG. 2, a large zone 12, which is poor in charge carriers, is formed also in the case of the semiconductor-diode detector, by high voltage in the non-conducting direction of the diode, within which zone a measurable flow of current is produced upon the entrance of ionizing radiation as a result of the formation of pairs of charge carriers, which flow of current can be measured in a sensitive ammeter 11. This flow of current again reflects the intensity of the radiation.

Figure 4:
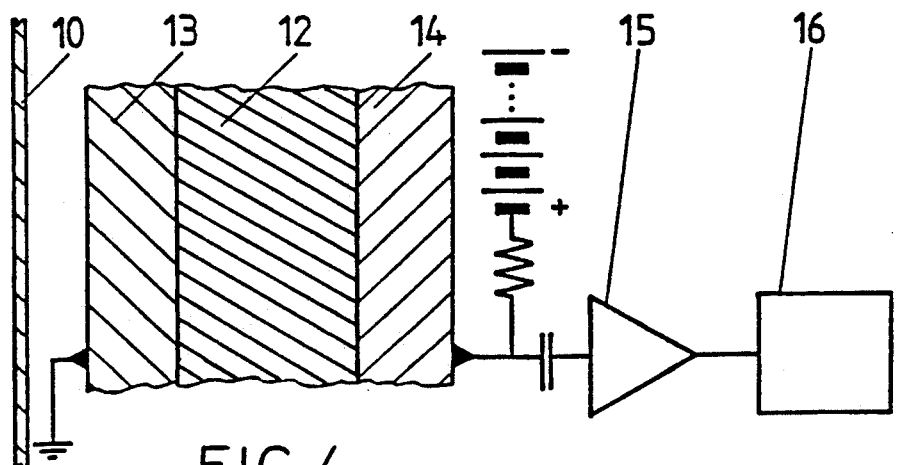
FIG. 4 is a cross section through a semiconductor-diode detector with pulse discrimination.

FIG. 4 also shows a semiconductor detector, the internal structure of which corresponds to FIG. 3. A sensitive amplifier 15 coupled to the semiconductor detector provides pulses from the detector which can readily be processed electronically. The amplitudes of these pulses reflect the energy of the individual radiation quanta (of the ionizing radiation). The selective sensitivity of the detector is obtained by the electronic selection of the pulse heights in a single-channel discriminator 16.

The manner of operation is as follows:

The material 6 to be measured, i.e. the zinc-coated steel, is irradiated with X-rays from the X-ray tube 2 and excited to emit X-ray fluorescence lines. These fluorescence lines are the so-called characteristic K radiation of zinc and iron. These fluorescence radiations are detected by detectors 3 and 4, and optionally 5, which are arranged in the indicated angular ranges alpha, beta and gamma. The detectors 3 and 5, in front of which, for instance, a copper metallic foil 10 is present as an absorption filter, is mounted at a small angle alpha of at most 30° to the material 6 being measured. Due to the small angle, the zinc radiation excited in the material 6 being measured accordingly has to pass over very long paths in the material 6 and thereby undergoes, within the measurement material 6 itself, an attenuation which is practically independent of the thickness of the zinc layer of the material 6. This has the result that the detector 3 or 5 in first approximation records only the iron content of the coating. The other detector 4 is positioned at an angle beta of 60° to 120° to the material 6 being measured in order to obtain the greatest possible depth of penetration of the observation. In front of this detector 4, there is present, for instance, a metal foil 10 of iron as the absorption filter so that the detector is adapted to detect the iron radiation. The weakening of the intensity of the ionizing radiation in the thickness of the coating is measured in this detector 4 and gives, in first approximation, the amount of zinc per unit of surface of the coating.

For the exact determination of the measurement values for the amount of zinc per unit of surface and the percentage of iron content in the coating, the signals from the above-mentioned detectors 3 and 4 are subjected to a mathematical algorithm in which the percentage of Fe in the Zn layer is a function of the ratio of the iron content to the amount of Zn per unit area. These signals are processed in known electronic data processing devices 17, displayed and/or recorded, and used for controlling the manufacturing process.

Should tilting or fluttering movements of the material 6 being measured take place during the course of the production as a result of certain production circumstances, so that inaccuracies in measurement may be possible, these measurement inaccuracies can be eliminated by the provision of the third detector 5. This third detector 5 must be arranged symmetrically to the detector 3, i.e. at the same angle alpha to the material 6 being measured, so that, for instance, upon tilting of the material 6 being measured in counterclockwise direction, the detection of the smaller measurement value by the detector 3 is eliminated by the detection of a larger measurement value by the detector 5.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. Apparatus for measuring at least one of the iron content and thickness of a layer containing zinc, the layer disposed on a base containing iron, the iron base with the zinc layer thereon being disposed in a plane, the apparatus comprising a source of X-radiation arranged at an angle of between approximately 60° and 120° to the plane of the iron base with the zinc layer thereon and for irradiating the iron base with the zinc layer thereon with said X-radiation, at least two detectors each having selective sensitivity for detecting radiation emitted by said iron base with the zinc layer thereon in response to said X-radiation, the first detector being arranged at an angle of at most 30° to said plane and the second detector being arranged at an angle of between approximately 60° and 120° to said plane.

2. Apparatus as recited in claim 1, further comprising a third detector, said third detector being arranged at the same angle to the plane as said first detector.

3. Apparatus as recited in claim 2, wherein the detectors are each provided with an absorption filter for providing selective sensitivity to the detector.

4. Apparatus as recited in claim 3, wherein said absorption filter comprises a metal foil.

5. Apparatus as recited in claim 3, wherein at least one of the detectors comprises a semiconductor-diode detector connected to a sensitive amplifier, pulses from said detectors being supplied to said amplifier, the amplified pulses being electronically selectable in a single-channel discriminator in order to obtain the selective sensitivity.

6. Apparatus as recited in claim 3, wherein at least one of said detectors comprises an ionization chamber.

7. Apparatus as recited in claim 2, further comprising means for processing signals from said detectors and for displaying measurement results.

8. Apparatus as recited in claim 7, further comprising means for controlling a process of manufacturing galvanized steel or galvannealed steel using said measurement results.

9. Apparatus receiving a material comprising a layer on a base, and for measuring the percentage content of a first component in the layer, the layer comprising primarily a second component and being disposed in a plane, the base comprising at least in part the first component, the apparatus comprising:

means for producing radiation and directing said radiation at said material such that said radiation will excite said material to produce characteristic emissions at particular frequencies for each of the first and second components, said means for producing radiation being disposed at a first specified angle to the plane of said material;

a first detector disposed at a second specified angle, said first detector receiving said characteristic emissions from said material such that a characteristic emission from said second component is substantially damped in said material, and such that said first detector detects substantially only a characteristic emission from said first component, thereby detecting the amount of said first component in said layer;

a second detector disposed at a third specified angle for receiving and detecting and characteristic emissions from said material such that said characteristic emission from said first component is damped, and such that said second detector detects substantially only a characteristic emission from said second component, the amount of said damping being related to and determining substantially the amount of said second component in said material; and means receiving signals from said first and second detectors for determining the percentage of said first component in said layer as a function of said signals.

10. Apparatus as recited in claim 9, wherein said means for producing radiation comprises a source of X-ray radiation.

11. Apparatus as recited in claim 9, wherein said first detector is disposed at said second specified angle such that the characteristic emission from said second component is substantially damped due to the relatively long distance said characteristic emission travels in said material.

12. Apparatus as recited in claim 11, wherein said second specified angle is no more than 30° to the plane of said material.

13. Apparatus as recited in claim 10, wherein said first specified angle is between approximately 60° and 120° to the plane of said material.

14. Apparatus as recited in claim 11, wherein said second detector is disposed at said third specified angle such that characteristic emissions from said material travel a shorter distance through said material than emissions travelling to said first detector.

15. Apparatus as recited in claim 14, wherein said third specified angle is between approximately 60° and 120° to the plane of said material.

16. Apparatus as recited in claim 9, further comprising a third detector, said third detector also being arranged such that the characteristic emission from said second component is substantially attenuated whereby said third detector detects substantially only the characteristic emission from said first component.

17. Apparatus as recited in claim 16, wherein said third detector is disposed at an angle of at most 30° to the plane of said material.

18. Apparatus as recited in claim 9, wherein said material is galvanized steel or galvannealed steel and said second component comprises zinc and said first component comprises iron.

19. A method for measuring the percentage content of a first component in a layer disposed on a base, the layer comprising primarily a second component, the base comprising at least in part the first component, the layer and base together comprising sheet material disposed in a plane, the method comprising:

producing radiation and directing said radiation at said material such that said radiation will excite said material to produce characteristic emissions at particular frequencies for each of the first and second components, said step of directing comprising directing the radiation at a first specified angle to the plane of said material;

receiving said characteristic emissions from said material at a first location at a second specified angle, such that a characteristic emission from said second component is substantially damped in said material, and such that substantially only a characteristic emission from said first component and thereby the amount of said first component in said layer is detected;

receiving and detecting said characteristic emissions from said material at a second location at a third specified angle such that the characteristic emission from said first component is damped, and such that substantially only a characteristic emission from said second component is detected, the amount of said damping being related to and determining substantially the amount of said second component in said material; and determining from the amount of said first component in said layer and the amount of said second component the percentage of said first component in said layer.

20. Method as recited in claim 19, wherein said step of producing radiation comprises producing X-ray radiation.

21. Method as recited in claim 19, wherein said second specified angle is such that the characteristic emission from said second component is substantially damped due to the relatively long distance said characteristic emission travels in said material.

22. Method as recited in claim 21, wherein said second specified angle is no more than 30° to the plane of said material.

23. Method as recited in claim 20, wherein said first specified angle is between approximately 60° and 120° to the plane of said material.

24. Method as recited in claim 19, wherein said third specified angle is such that characteristic emissions from said material travel a shorter distance through said material than radiation travelling through said material at said second specified angle.

25. Method as recited in claim 24, wherein said third specified angle is between approximately 60° and 120° to the plane of said material.

26. Method as recited in claim 19, further comprising receiving said characteristic emissions at a third location such that the characteristic emission from said second component is substantially attenuated whereby substantially only the characteristic emission from said first component is detected at said location.

27. Method as recited in claim 26, wherein said step of receiving characteristic emissions at said third location comprises receiving said emissions at an angle of at most 30° to the plane of said material.

28. Method as recited in claim 19, wherein said material is galvanized steel or galvannealed steel and said first component comprises iron and said second component comprises zinc.

29. Method as recited in claim 28, wherein said third located is disposed substantially opposite said first location, at the same angle above the plane of the material as said first location whereby, if said material is rotated out of said plane, one of said locations will detect more characteristic emissions from said material and said other location will detect less characteristic emissions from said material.

* * * * *